(12) United States Patent
Thoreson

(10) Patent No.: US 6,439,886 B1
(45) Date of Patent: Aug. 27, 2002

(54) INFLATABLE DENTAL DEVICE

(76) Inventor: Mark G. Thoreson, 1680 Chamgers St., Eugene, OR (US) 97402

( * ) Notice: Subject to any disclaimer, the term of this patent is extended or adjusted under 35 U.S.C. 154(b) by 0 days.

(21) Appl. No.: 09/642,442

(22) Filed: Aug. 23, 2000

(51) Int. Cl.[7] ................................. A61C 5/04
(52) U.S. Cl. ............................ 433/155; 433/39
(58) Field of Search ............... 433/39, 40, 155, 433/68, 72, 136

(56) References Cited

U.S. PATENT DOCUMENTS

| | | | |
|---|---|---|---|
| 3,863,343 A | * 2/1975 | Malmin | 433/136 |
| 4,259,070 A | 3/1981 | Soelberg et al. | 433/149 |
| 4,917,646 A | 4/1990 | Kleves | 446/224 |
| 5,527,181 A | 6/1996 | Rawls et al. | 433/149 |
| 5,573,400 A | 11/1996 | Asher | 433/136 |
| 6,007,334 A | * 12/1999 | Suhonen | 433/39 |
| 6,206,697 B1 | * 3/2001 | Hugo | 433/39 |

* cited by examiner

*Primary Examiner*—Todd E. Manahan
(74) *Attorney, Agent, or Firm*—James D. Givnan, Jr.

(57) ABSTRACT

A device having pliable walls is provided for placement in the mouth of a patent to serve, in one manner, as a matrix barrier with walls of the device bearing upon opposed tooth surfaces. An inlet permits inflation of the device, as by a dental syringe, of the installed device. A valve closes under air pressure to seal the inlet which may also be closed by a fused inlet segment.

11 Claims, 2 Drawing Sheets

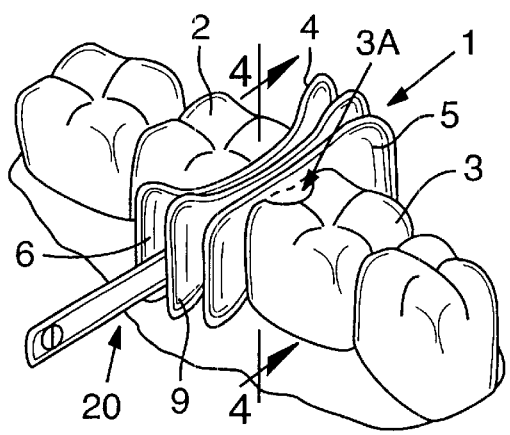
FIG. 1
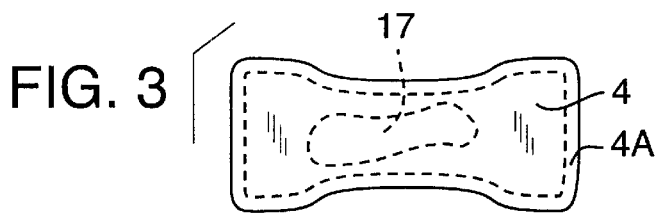
FIG. 3
FIG. 2
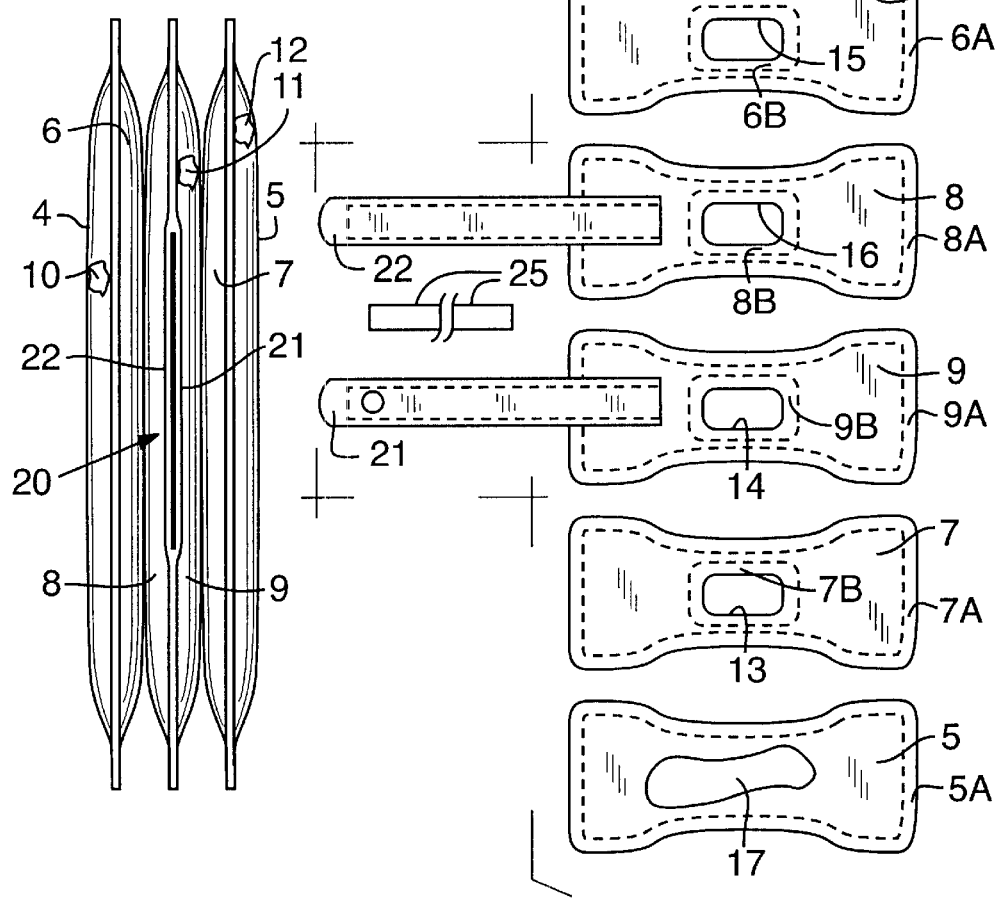

INFLATABLE DENTAL DEVICE

BACKGROUND OF THE INVENTION

The present invention concerns generally an inflatable device primarily for placement intermediate adjacent teeth preparatory to the insertion of filling material.

Matrix barriers as used in dentistry include a metal band and a screw down tensioning device and have been in use for many years for confining filling or matrix material. Installation of conventional matrix barriers is time consuming and renders the patient's gum or lip subject to being pinched upon tightening of the screw mechanism. Further, wedges may be required to enhance engagement of the matrix band with the tooth being filled to provide the necessary sealing effect. At completion of use, the conventional matrix band or retainer is removed from the tooth by unscrewing of the mechanism which must be subsequently autoclaved. The metal matrix band is dispensed with after use. Accordingly, retention of matrix material in a prepared tooth entails a considerable effort and time in installation and removal, is costly and may subject the patient to a pinched gum or lip. Further, it is often necessary to utilize a dental wedge along with a matrix band to achieve desired band-to-tooth securement resulting in further discomfort to the patient.

SUMMARY OF THE PRESENT INVENTION

The present invention is directed toward the provision of an inflatable dental device primarily for installation between adjacent teeth to serve as a retainer to confine matrix material at the prepared location in a tooth. Additional uses of the inflatable device may encompass securing of a dam in place in the mouth or to retain facial tissue away from a work site.

The present device is of pliable material with a fused or heat sealed perimeter defining an air chamber which, upon inflation, biases outermost wall surfaces of the device into engagement with interproximal tooth surfaces. The device, when used as a matrix barrier, is readily insertable between adjacent teeth in view of a thin cross section consisting of plies of synthetic material in sheet form fused at their perimeters. An inlet receives a pressurized flow during inflation of the barrier with closure means maintaining the barrier in an inflated state. A valve may be utilized or the neck may be heat sealed upon inflation. Subsequent to use, the device is readily removed upon deflation as by puncturing of same. Inflation of the barrier may be by use of a three way dental syringe as adequate air pressure is available in most dental facilities.

Important objectives of the present dental device include use as an inflatable barrier which may be readily placed between teeth and subsequently inflated to provide a seal against composite filing material subsequently deposited in the tooth; the provision of an inflated matrix barrier for contact with the edges of the cavo surface of a tooth being restored to reduce trimming or touch-up efforts of the deposited material upon barrier removal; the provision of a readily usable matrix barrier utilizing readily available air pressure which ultimately permits barrier removal simply by puncturing of the disposable barrier; the provision of a matrix barrier of the single use or throw away type to reduce autoclaving efforts; the provision of an inflatable device for securing a rubber dam in place in the mouth or as a retraction device for the tongue or cheek retention.

BRIEF DESCRIPTION OF THE DRAWINGS

In the accompanying drawings:

FIG. 1 is a perspective view of the present dental device operatively disposed between adjacent teeth as a matrix barrier;

FIG. 2 is an end elevational view taken from the left hand side of the barrier of FIG. 1 partially inflated for illustrative purposes;

FIG. 3 is an exploded view of the device;

DETAILED DESCRIPTION OF THE PREFERRED EMBODIMENTS

Figure 4:
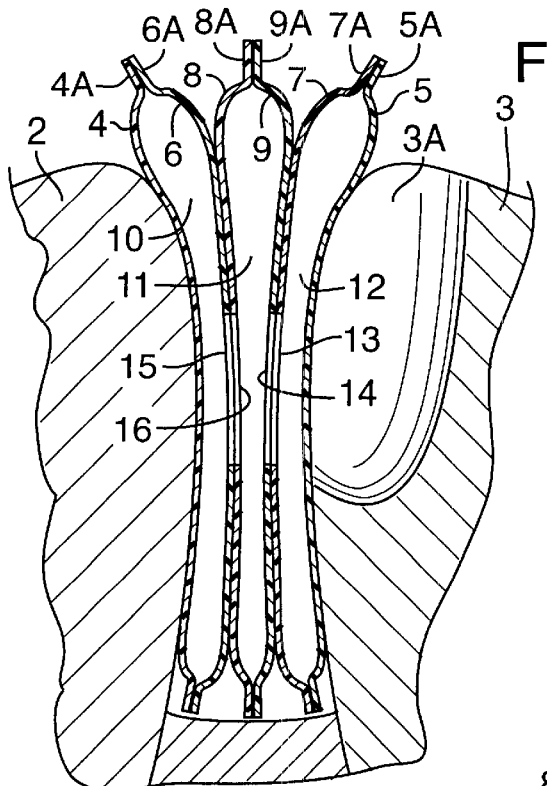
FIG. 4 is a vertical sectional view of the device taken along line 4—4 of FIG. 1.

With continuing attention to the drawing wherein applied reference numerals indicate parts similarly hereinafter identified, the reference numeral 1 indicates generally the present device disposed between adjacent teeth 2 and 3 of a dental patient. A matrix receiving site 3A has been formed in tooth 3. Device outer walls at 4 and 5 are disposed for biased contact with interproximal tooth surfaces upon inflation of the device. Outer walls 4 and 5 each have a companion wall as at 6 and 7. Wall marginal areas at 4A–6A and 5A–7A are joined as by fusing. An inner pair of walls at 8 and 9 are similarly joined at their outer marginal areas at 8A and 9A. Accordingly, chambers at 10, 11 and 12 are provided with communication therebetween as follows.

Walls 6 and 8 and 7 and 9 have fused inner areas at 6B, 8B and at 7B, 9B respectively which define corresponding openings 14–15 in the walls for the passage of a pressurized medium between the wall defined chambers.

While multiple sets of walls are above noted, in some instances a single set of walls may be adequate with the chamber defined thereby in direct communication with an inlet as later described.

Suitable material for the walls may be very thin nylon sheets each having a polyethylene layer enabling joining of the above mentioned areas by heat a combination found in metallic coated, non-latex balloon construction. Surface coatings at 17 in place on outer walls 4 and 5 serve to reflect light wave energy for curing of composite matrices.

Figure 5:
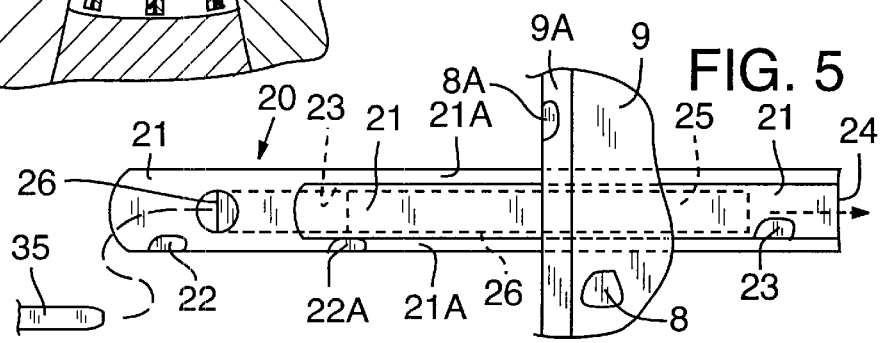
FIG. 5 is an enlarged plan view of a device fragment and inlet extending therethrough.

For charging the device with a pressurized fluid an inlet, generally at 20, is provided. As best shown in FIG. 5, the inlet is formed from two elongate plies 21–22, heat sealed together along their corresponding sides or edges 21A–22A to form a passageway 23 terminating at an outlet end 24 interiorly in center chamber 11. To maintain passageway 23 open during heat sealing of the inlet plies, a heat resistant strip 25 extends from an air inlet opening 26, between ply 22 and the strip, and along passageway 23 to a point beyond where inlet 20 intersects fused margins 8A and 9A of walls 8 and 9 defining centrally disposed chamber 11. U.S. Pat. No. 4,917,646 is incorporated herein by reference and discloses a self-sealing valve in conjunction with balloon construction.

Figure 6:
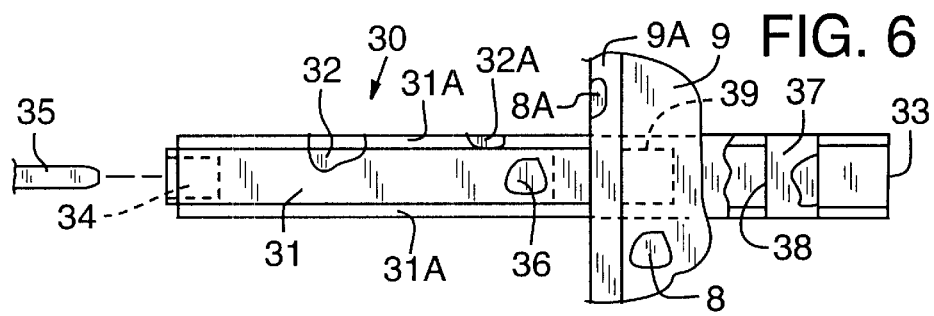
FIG. 6 is a plan view of a modified inlet component.

In FIG. 6, a modified inlet generally at 30 is shown having plies 31–32 fused along their corresponding edges 31A–32A providing a passageway 36 and which fuse with fused edges 8A–9A of the inner pair of walls 8 and 9 and provide an outlet 33 in communication with central chamber 11. An inlet opening at 34 receives the nozzle 35 of a three-way dental syringe for purposes of inflation. Inlet 30 may rely on a folded or flap valve at 37 folded at 38 and closed by chamber pressure bearing upon the plies 31–32 to urge a free end of the valve at 37 to close against the plies. A heat resistant strip at 39 prevents fusing of plies 31–32 during fusing of marginal areas 8A–9A of the device.

Figure 7:
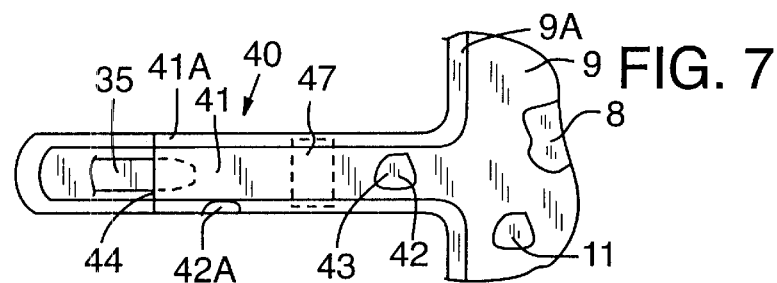
FIG. 7 is a plan view of still another form of inlet.

In FIG. 7 a further modified inlet is shown generally at 40. Inlet plies are at 41–42 having marginal edges 41A–42A fused to define a passageway 43. A slit 44 in ply 41 permits insertion of syringe nozzle 35 for inflation of chamber 11 defined by walls 8 and 9.

Upon inflation of the device, a heat source with heated, biased members pinches plies 41 and 42 together resulting in fusing and in closure of passageway 43 at an area indicated at 47.

The present device is approximately one inch by one-half inch excluding the inlet, for use in the mouth of an adult and of somewhat lesser size for a younger person. Inflation of the device will require a source of air pressure in the range of 20 psi –40 psi.

The device is flat prior to inflation with the combined layers or walls of nylon material of a cross section permitting insertion between teeth prior to inflation and after tooth preparation. If simultaneously used to hold or stabilize a rubber dam, the device will be placed prior to tooth preparation. The dental auxiliary may, if necessary, maintain the device in place during inflation as by a three-way syringe. The device will expand to its fully inflated shape to retain its position. The use of reflective coating 17 on the surface proximate the prepared area of the tooth will assist in proper curing of the composite materials by reflection of high-intensity curing light.

With the device in the proper position, the composite materials are deposited, manipulated and cured as usual per the clinician's chosen protocol. The seal achieved at the edges of the preparation (the cavosurface) minimizes trimming or touch-up. When completed, the device is punctured with a sharp instrument and withdrawn from between the teeth. The final steps, verification and adjustment of the bite, polishing and a final sealer are then completed as usual.

While I have shown but a few embodiments of the invention, it will be apparent to those skilled in the art that the invention may be embodied still otherwise without departing from the spirit and scope of the claimed invention.

Having thus described the invention, what is desired to be secured by a Letters Patent is:

1. An inflatable matrix barrier for placement in a patient's mouth, said matrix barrier comprising,
   pliable walls having joined marginal areas to define at least one chamber for reception of a pressurized medium, said pliable walls including outer walls for contact with interproximal surface of adjacent teeth,
   an inlet for the medium in communication with the chamber, and
   closure means for restricting flow of a medium through said inlet subsequent to inflation of the device.

2. The inflatable matrix barrier claimed in claim 1 wherein said pliable walls have marginal areas fused at corresponding marginal areas.

3. The inflatable matrix barrier claimed in claim 2 wherein said pliable walls define multiple chambers, openings in some of said walls in register with one another communicating said chambers.

4. The inflatable matrix barrier claimed in claim 3 wherein said some of said pliable walls have internal marginal areas defining said openings, said internal marginal areas fused to other of said marginal areas.

5. The inflatable matrix barrier claimed in claim 3 wherein one of said outer walls includes a light reflecting surface to facilitate curing of matrix in a tooth.

6. The inflatable matrix barrier claimed in claim 1 wherein said inlet is of tubular construction, said closure means includes a pressurized medium in said chamber biasing said inlet to a closed state.

7. The inflatable matrix barrier claimed in claim 6 wherein said inlet includes elongate plies, said closure means include fused segments of said plies.

8. A dental matrix retainer including,
   an inflatable body having multiple juxtaposed walls joined at their margins for placement in contact with interproximal tooth surfaces with one of the surfaces defining a matrix receiving site, said inflatable body defining a chamber
   inlet means in communication with said chamber for directing a pressurized fluid flow thereto, and
   closure means in said inlet means for closing said inlet means to retain the inflatable body in an inflated state and in biased contact with tooth surfaces for matrix retention.

9. The matrix retainer claimed in claim 8 wherein said inflatable body defines multiple chambers.

10. The matrix retainer claimed in claim 9 wherein said inflatable body includes multiple pliable walls each having an outer marginal area fused to the outer marginal area of an adjacent one of said walls.

11. The matrix retainer claimed in claim 10 wherein some of said pliable walls have internal marginal areas defining openings fused to other of said internal marginal areas defining openings to communicate said multiple chambers.

* * * * *